(12) United States Patent
Fryburg et al.

(10) Patent No.: US 6,610,746 B2
(45) Date of Patent: Aug. 26, 2003

(54) SYNERGISTIC EFFECT OF A SULFONYLUREA AND/OR NON-SULFONYLUREA K+ATP CHANNEL BLOCKER, AND A PHOSPHODIESTERASE 3 TYPE INHIBITOR

(75) Inventors: David A. Fryburg, East Lyme, CT (US); Janice C. Parker, Ledyard, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/829,874

(22) Filed: Apr. 10, 2001

(65) Prior Publication Data

US 2002/0013268 A1 Jan. 31, 2002

Related U.S. Application Data

(60) Provisional application No. 60/196,728, filed on Apr. 13, 2000.

(51) Int. Cl.$^7$ .................. A61K 31/64; A61K 38/28
(52) U.S. Cl. .................. 514/592; 514/3; 514/350; 514/352; 514/356; 514/396; 514/592
(58) Field of Search ................ 514/3, 350, 352, 514/396, 357, 592, 600

(56) References Cited

FOREIGN PATENT DOCUMENTS

WO          WO9836755          8/1998 .......... A61K/31/64

OTHER PUBLICATIONS

Fujimoto, S., et al., The Novel Insulinotropic Mechanism of Pimobendan: Direct Enhancement of the Exocytotic Process of Insulin Secretory Granules by Increased $Ca^2$ Sensitivity in β–Cells, *Endocrinology,* vol. 139, No. 3, pp. 1133–1140.

Hohn, H., et al., Potential Antidiabetic Agents. Pyrazolo[3, 4–b]pyridines, *Journal of Medicinal Chemistry,* vol. 16, No. 12, pp. 1340–1346, (1973).

Grill, V., et al., Interacting Effects of Sylfonylureas and Glucose on Cyclic AMP Metabolism and Insulin Release in Pancreatic Isle of the Rat, *J. Clin. Invest.,* vol. 61, No. 5, pp. 1346–1354, (1978).

Parker, J. C., et al., Effects of Cyclic AMP Phosphodiesterase Inhibitors on Insulin Secretion and Glycemia, *Diabetologia,* vol. 39, Suppl. 1, p. A225, Sep. 1, 1996.

J. C. Parker, et al. Cycluc AMP Phosphodiesterases of Human and Rat Islets of Langerhans: Contributions of Types III and IV to the Modulation of Insulin Secretion, *Biochemical and Biophysical Research Communictions.* Dec. 26, 1995. vol. 217, No. 3. pp. 816–923.

M. El–Metwally, et al. The Effect of selective phosphodiesterase inhibitors on plasma insulin concentration and insulin secretion in vitro in the rat. *European Journal of Pharmacology.* 1997. vol. 324. pp. 227–232.

J. C. Parker, et al. Modulation of Insulin Secretion and Glycemia by Selective Inhibition of Cyclic AMP Phosphodiesterase III. *Biochemical and Biophysical Research Communications.* 1997. vol. 236. Article No. RC977034. pp. 665–669.

M.D. Leibowitz, et al. A Novel Insulin Secretagogue Is a Phosphodiesterase Inhibitor. *Diabetes.* Jan. 1995. vol. 44. pp. 67–74.

*Primary Examiner*—Christopher S. F. Low
*Assistant Examiner*—Chih-Min Kam
(74) *Attorney, Agent, or Firm*—Peter C. Richardson; Gregg C. Benson; Carl J. Goddard (57) ABSTRACT

The present invention provides methods of treating non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance, the methods comprising the step of administering to a patient having or at risk of having non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance a synergistic amount of:1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor. The present invention also provides kits and pharmaceutical compositions that comprise: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor. The present invention also relates to kits and pharmaceutical compositions that comprise 1) a sulfonylurea, a non-sulfonylurea $K^+$ ATP channel blocker, or a sulfonylurea and a non-sulfonylurea $K^+$ ATP channel blocker; 2) a cAMP phosphodiesterase type 3 inhibitor; and 3) an additional compound useful for the treatment of non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance.

8 Claims, 1 Drawing Sheet

Figure 1. Isobologram showing the synergistic effect of glyburide and milrinone

SYNERGISTIC EFFECT OF A SULFONYLUREA AND/OR NON-SULFONYLUREA K+ATP CHANNEL BLOCKER, AND A PHOSPHODIESTERASE 3 TYPE INHIBITOR

CROSS-REFERENCE TO RELATED APPLICATION

This application claims priority of U.S. provisional application No. 60/196,728, filed Apr. 13, 2000.

FIELD OF THE INVENTION

The present invention relates to methods of treating non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance, the methods comprising the step of administering to a patient having or at risk of having non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance a synergistic amount of: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor. The present invention also relates to kits and pharmaceutical compositions that comprise: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor. The present invention also relates to kits and pharmaceutical compositions that comprise: 1) a sulfonylurea, a non-sulfonylurea $K^+$ ATP channel blocker, or a sulfonylurea and a non-sulfonylurea $K^+$ ATP channel blocker; 2) a cAMP phosphodiesterase type 3 inhibitor; and 3) an additional compound useful for the treatment of non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance.

BACKGROUND OF THE INVENTION

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes can be improved.

A group of compounds that stimulate insulin secretion and stimulate de novo synthesis of insulin are the cAMP phosphodiesterase type 3 inhibitors. It is believed that cAMP phosphodiesterase type 3 inhibitors act to increase insulin secretion by increasing intracellular levels of cAMP in pancreatic β-cells in the islet of Langerhans. In contrast, sulfonylureas act on the $K^+$ ATP channels of pancreatic β-cells in the islet of Langerhans. Moreover, cAMP phosphodiesterase type 3 is known to exist in two forms: type A and type B. Type A cAMP phosphodiesterase 3 is associated with cardiac tissue and with platelets, and type B is associated with liver and adipose tissue, and β-cells in the pancreas.

In addition to sulfonylureas, which stimulate insulin secretion by acting on the $K^+$ ATP channels, a group of non-sulfonylureas are known to stimulate insulin secretion by acting on $K^+$ ATP channels. Examples of such non-sulfonylurea insulin secretagogues include nateglinide and repaglinide.

The present invention provides an improved method of treating non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance using a synergistic amount of: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor.

The present invention also relates to kits and pharmaceutical compositions that comprise: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor.

In addition, the present invention relates to kits and pharmaceutical compositions that comprise: 1) a sulfonylurea, a non-sulfonylurea $K^+$ ATP channel blocker, or a sulfonylurea and a non-sulfonylurea $K^+$ ATP channel blocker; 2) a cAMP phosphodiesterase type 3 inhibitor; and 3) an additional compound useful for the treatment of non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance.

SUMMARY OF THE INVENTION

The present invention provides methods of treating non-insulin dependent diabetes mellitus, the methods comprising the step of administering to a patient having or at risk of having non-insulin dependent diabetes a synergistic amount of: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor.

Also provided are methods of treating insulin resistance, the methods comprising the step of administering to a patient having or at risk of having insulin resistance a synergistic amount of: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor.

Also provided are methods of treating Syndrome X, the methods comprising the step of administering to a patient having or at risk of having Syndrome X a synergistic amount of: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor.

Also provided are methods of treating diabetic neuropathy, diabetic nephropathy, diabetic retinopathy, diabetic cardiomyopathy, polycystic ovary syndrome, or cataracts, the methods comprising the step of administering to a patient having or at risk of having diabetic neuropathy, diabetic nephropathy, diabetic retinopathy, diabetic cardiomyopathy, polycystic ovary syndrome, or cataracts a synergistic amount of: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor.

Also provided are methods of treating hyperglycemia, the methods comprising the step of administering to a patient having or at risk of having hyperglycemia a synergistic amount of: 1) a sulfonylurea, a non-sulfonylurea K$^+$ ATP channel blocker, or a sulfonylurea and a non-sulfonylurea K$^+$ ATP channel blocker; and 2) a cAMP phosphodiesterase type 3 inhibitor.

Also provided are methods of treating impaired glucose tolerance, the methods comprising the step of administering to a patient having or at risk of having impaired glucose tolerance a synergistic amount of: 1) a sulfonylurea, a non-sulfonylurea K$^+$ ATP channel blocker, or a sulfonylurea and a non-sulfonylurea K$^+$ ATP channel blocker; and 2) a cAMP phosphodiesterase type 3 inhibitor.

Also provided are pharmaceutical compositions comprising a sulfonylurea and/or non-sulfonylurea K$^+$ ATP channel blocker, and a cAMP phosphodiesterase type 3 inhibitor.

Also provided are pharmaceutical compositions comprising a sulfonylurea and a cAMP phosphodiesterase type 3 inhibitor.

Also provided are pharmaceutical compositions comprising a non-sulfonylurea K$^+$ ATP channel blocker and a cAMP phosphodiesterase type 3 inhibitor.

Also provided are pharmaceutical compositions comprising a sulfonylurea, a non-sulfonylurea K$^+$ ATP channel blocker, and a cAMP phosphodiesterase type 3 inhibitor.

Also provided are kits for the treatment of non-insulin dependent diabetes mellitus, the kits comprising:
a) a first pharmaceutical composition comprising: 1) a sulfonylurea, a non-sulfonylurea K$^+$ ATP channel blocker, or a sulfonylurea and a non-sulfonylurea K$^+$ ATP channel blocker; and 2) a cAMP phosphodiesterase type 3 inhibitor;
b) a second pharmaceutical composition comprising a second compound useful for the treatment of non-insulin dependent diabetes mellitus; and
c) a container for the first and second compositions.

In a preferred embodiment of the kits, the second compound is selected from:
insulin and insulin analogs;
GLP-1 (7-37) (insulinotropin) and GLP-1 (7-36)-NH$_2$;
biguanides;
glycogen phosphorylase inhibitors;
aldose reductase inhibitors;
α2-antagonists;
imidazolines;
glitazones (thiazolidinediones);
PPAR-gamma agonists;
fatty acid oxidation inhibitors;
α-glucosidase inhibitors;
β-agonists;
lipid-lowering agents;
antiobesity agents;
vanadate, vanadium complexes and peroxovanadium complexes;
amylin antagonists;
glucagon antagonists;
gluconeogenesis inhibitors;
somatostatin agonists and antagonists; or
antilipolytic agents.

In a more preferred embodiment of the kits, the second compound is selected from LysPro insulin, GLP-1 (7-37) (insulinotropin), GLP-1 (7-36)-NH$_2$, metformin, phenformin, buformin, midaglizole, isaglidole, deriglidole, idazoxan, efaroxan, fluparoxan, linogliride, ciglitazone, pioglitazone, englitazone, troglitazone, darglitazone, rosiglitazone, clomoxir, etomoxir, acarbose, miglitol, emiglitate, voglibose, MDL-25,637, camiglibose, MDL-73, 945, BRL 35135, BRL 37344, Ro 16-8714, ICI D7114, CL 316,243, benfluorex, fenfluramine, Naglivan®, acipimox, WAG 994, Symlin™, or AC2993.

In another preferred embodiment of the kits, the second compound is selected from insulin, biguanides, or thiazolidinediones.

Also provided are kits for the treatment of non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance, the kits comprising:
a) a first pharmaceutical composition comprising: 1) a sulfonylurea, a non-sulfonylurea K$^+$ ATP channel blocker, or a sulfonylurea and a non-sulfonylurea K$^+$ ATP channel blocker; and 2) a cAMP phosphodiesterase type 3 inhibitor;
b) a second pharmaceutical composition comprising a second compound useful for the treatment of non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance; and
c) a container for the first and second compositions.

Also provided are kits for the treatment of non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance, the kits comprising:
a) a first pharmaceutical composition comprising a sulfonylurea or a non-sulfonylurea K$^+$ ATP channel blocker;
b) a second pharmaceutical composition comprising a cAMP phosphodiesterase type 3 inhibitor; and
c) a container for the first and second compositions.

In a preferred embodiment of the methods, kits, and pharmaceutical compositions, the sulfonylurea is glyburide and the cAMP phosphodiesterase type 3 inhibitor is milrinone.

In another preferred embodiment of the methods, kits, and pharmaceutical compositions, the cAMP phosphodiesterase type 3 inhibitor is a selective cAMP phosphodiesterase type 3B inhibitor.

In another preferred embodiment of the methods, kits, and pharmaceutical compositions, the sulfonylurea is glyburide, chlorpropamide, glibenclamide, glipizide, gliclazide, glimepiride, tolbutamide, acetohexamide, or tolazamide.

In another preferred embodiment of the methods, kits, and pharmaceutical compositions, the sulfonylurea is glipizide or glyburide.

In another preferred embodiment of the methods, kits, and pharmaceutical compositions, the sulfonylurea is glyburide.

In another preferred embodiment of the methods, kits, and pharmaceutical compositions, the cAMP phosphodiesterase type 3 inhibitor is milrinone, amrinone, enoximone, indolidan, cilostamide, lixazinone, imazodan, cilostazol, bemorandan, siguazodan, adibendan, pimobendan, saterinone, sulmazol, or vesnarinone.

In another preferred embodiment of the methods, kits, and pharmaceutical compositions, the cAMP phosphodiesterase type 3 inhibitor is milrinone.

In another preferred embodiment of the methods, kits, and pharmaceutical compositions, the cAMP phosphodiesterase type 3 inhibitor is milrinone and the sulfonylurea is glyburide.

In another preferred embodiment of the methods, kits, and pharmaceutical compositions, the non-sulfonylurea K$^+$ ATP channel blocker is repaglinide or nateglinide.

DETAILED DESCRIPTION OF THE INVENTION

The present invention provides methods of treating non-insulin dependent diabetes mellitus, insulin resistance, Syndrome X, diabetic neuropathy, diabetic nephropathy, diabetic retinopathy, diabetic cardiomyopathy, diabetic cardiomyopathy, polycystic ovary syndrome, cataracts, hyperglycemia, or impaired glucose tolerance, the methods comprising the step of administering to a patient having or at risk of having non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance a synergistic amount of: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor.

The present invention also provides kits and pharmaceutical compositions that comprise: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor.

In addition, the present invention provides kits and pharmaceutical compositions that comprise: 1) a sulfonylurea, a non-sulfonylurea $K^+$ ATP channel blocker, or a sulfonylurea and a non-sulfonylurea $K^+$ ATP channel blocker; 2) a cAMP phosphodiesterase type 3 inhibitor; and 3) an additional compound useful for the treatment of non-insulin dependent diabetes mellitus, insulin resistance, Syndrome X, diabetic neuropathy, diabetic nephropathy, diabetic retinopathy, diabetic cardiomyopathy, polycystic ovary syndrome, cataracts, hyperglycemia, or impaired glucose tolerance.

Certain terms and phrases that are used in this application are defined below.

The phrase "synergistic amount" means that the therapeutic effect of a sulfonylurea and/or non-sulfonylurea $K^+$ ATP channel blocker, when administered in combination with a cAMP phosphodiesterase type 3 inhibitor, is greater than the predicted additive therapeutic effect of a sulfonylurea and/or a non-sulfonylurea $K^+$ ATP channel blocker, and a cAMP phosphodiesterase type 3 inhibitor when administered alone.

The phrase "therapeutic effect" means an amount of a compound or combination of compounds that treats a disease; ameliorates, attenuates, or eliminates one or more symptom of a particular disease; or prevents or delays the onset of one of more symptom of a particular disease.

The phrase "non-sulfonylurea $K^+$ ATP channel blocker" means a compound that is not a sulfonylurea, but acts like a sulfonylurea in that the compound is a $K^+$ ATP channel blocker. Examples of non-sulfonylurea $K^+$ ATP blockers include repaglinide and nateglinide.

The term "selective" with regard to CAMP phosphodiesterase type 3 inhibitors means that an inhibitor shows greater binding affinity with respect to one of the two types A and B. For example, a selective CAMP phosphodiesterase type 3B inhibitor has a higher binding affinity for CAMP phosphodiesterase type 3B than CAMP phosphodiesterase type 3A. In general, the affinity is about 50% greater for one type than the other type. More preferably, the affinity is about 75% greater, and most preferably is about 90% greater.

The term "patient" means animals, such as dogs, cats, cows, horses, sheep, and humans. Particularly preferred patients are mammals. The term patient includes males and females.

The phrase "pharmaceutically acceptable" means that the carrier, diluent, vehicle, excipients, and/or salt must be compatible with the other ingredients of the formulation, and not deleterious to the patient.

The terms "sulfonylurea," "non-sulfonylurea $K^+$ ATP channel blocker," and "cAMP phosphodiesterase type 3 inhibitor" and grammatical variations thereof, includes the stereoisomers of these compounds, pharmaceutically acceptable salts of the compounds, prodrugs of the compounds, and pharmaceutically acceptable salts of the prodrugs.

The terms "treating", "treat" or "treatment" include preventative (e.g., prophylactic) and palliative treatment.

Patients at risk for having non-insulin dependent diabetes mellitus include obese patients, patients having polycystic ovary syndrome, impaired glucose tolerance, insulin resistance, or having or having had gestational diabetes.

The sulfonylureas, non-sulfonylurea $K^+$ ATP channel blockers, and CAMP phosphodiesterase type 3 inhibitors of the present invention are administered to a patient in synergistic amounts. It has been surprisingly and unexpectedly discovered that administration of a combination of: 1) a sulfonylurea, a non-sulfonylurea $K^+$ ATP channel blocker, or a sulfonylurea and a non-sulfonylurea $K^+$ ATP channel blocker; and 2) a cAMP phosphodiesterase type 3 inhibitor results in greater therapeutic effect than the effect expected from the additive effects of each of the compounds. In addition, the present invention contemplates the use of both a sulfonylurea and a non-sulfonylurea $K^+$ ATP channel blocker along with a cAMP phosphodiesterase type 3 inhibitor. Also contemplated are the use of one or more sulfonylureas and/or one or more non-sulfonylurea $K^+$ ATP channel blockers in combination with one or more cAMP phosphodiesterase type 3 inhibitors.

The compounds can be administered alone or as part of a pharmaceutically acceptable composition or formulation. In addition, the sulfonylureas and/or non-sulfonylurea $K^+$ ATP channel blockers, and cAMP phosphodiesterase type 3 inhibitors can be administered all at once, as for example, by a bolus injection, multiple times, such as by a series of tablets, or delivered substantially uniformly over a period of time, as for example, using transdermal delivery. It is also noted that the dose of the sulfonylureas and/or non-sulfonylurea $K^+$ ATP channel blockers, and cAMP phosphodiesterase type 3 inhibitors can be varied over time.

In addition, the sulfonylureas, and/or non-sulfonylurea $K^+$ ATP channel blockers, and cAMP phosphodiesterase type 3 inhibitors of the present invention can be administered alone, in combination with other sulfonylureas, non-sulfonylurea $K^+$ ATP channel blockers, or cAMP phosphodiesterase type 3 inhibitors, or with other pharmaceutically active compounds. The other pharmaceutically active compounds can be intended to treat the same diseases as the sulfonylureas, non-sulfonylurea $K^+$ ATP channel blockers, or cAMP phosphodiesterase type 3 inhibitors or different diseases. If the patient is to receive or is receiving multiple compounds, the compounds can be administered simultaneously, or sequentially in any order. For example, in the case of tablets, the active compound(s) can be found in one tablet or in separate tablets, which can be administered at once or sequentially in any order. In addition, it should be recognized that the compositions can be different forms. For example, one or more compounds may be delivered via a tablet, while another is administered via injection or orally as a syrup. All combinations, delivery methods and administration sequences are contemplated.

Since the present invention contemplates the treatment of diseases with a combination of pharmaceutically active agents that can be administered separately, the invention further relates to combining separate pharmaceutical compositions in kit form. In one embodiment, a kit comprises two separate pharmaceutical compositions: one composition comprising a sulfonylurea and/or a non-sulfonylurea $K^+$ ATP channel blocker, and a cAMP phosphodiesterase type 3 inhibitor; and the second composition comprising a second pharmaceutically active compound. In another embodiment, a kit comprises two separate pharmaceutical compositions: one composition comprising a sulfonylurea and/or a non-sulfonylurea $K^+$ ATP channel blocker; and the second composition comprising a cAMP phosphodiesterase type 3 inhibitor. In still another embodiment, the kit comprises three separate pharmaceutical compositions: one composition comprising a sulfonylurea and/or a non-sulfonylurea $K^+$ ATP channel blocker; the second composition comprising a cAMP phosphodiesterase type 3 inhibitor; and the third composition comprising a third pharmaceutically active compound. Other kit variations for the sulfonylureas, non-sulfonylurea $K^+$ ATP channel blockers, and cAMP phosphodiesterase type 3 inhibitors are possible, and these variations are intended to be encompassed by the present invention. The kits also comprise a container for the separate compositions such as a divided bottle or a divided foil packet. Additional examples of containers include syringes, boxes, bags, and the like. Typically, the kits comprise directions for the administration of the separate components. The kit form is particularly advantageous when the separate components are preferably administered in different dosage forms (e.g., oral and parenteral), are administered at different dosage intervals, or when titration of the individual components of a combination of compounds is desired by the prescribing physician.

An example of such a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil that is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of a second compound can consist of several tablets or capsules and vice versa. The memory aid should reflect this and assist in correct administration of the compounds.

In another embodiment of the invention, a dispenser designed to dispense the daily doses one at a time in the order of their intended use is provided. Preferably, the dispenser is equipped with a memory aid, so as to further facilitate compliance with the dosing regimen. An example of such a memory aid is a mechanical counter that indicates the number of daily doses that have been dispensed. Another example of such a memory aid is a battery-powered microchip memory coupled with a liquid crystal readout, or audible reminder signal which, for example, reads out the date that the last daily dose has been taken and/or reminds a patient when the next dose is to be taken.

The sulfonylureas, non-sulfonylurea $K^+$ ATP channel blockers, and cAMP phosphodiesterase type 3 inhibitors of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. It is also noted that the administration methods include the use of controlled release compositions, including sustained release and delayed release, and immediate release compositions and combinations thereof.

Compositions suitable for parenteral injection may comprise physiologically acceptable sterile aqueous or nonaqueous solutions, dispersions, suspensions, emulsions, or sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, or by the use of surfactants.

These compositions may also contain adjuvants such as preserving, wetting, emulsifying, and dispersing agents. Microorganism contamination can be prevented by adding various antibacterial and antifungal agents to the compositions, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate or gelatin.

Solid dosage forms for oral administration include capsules, tablets, powders, and granules. In such solid dosage forms, the compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia;

(c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin or bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the compound or compounds in a certain part of the intestinal tract in a delayed manner. Examples of embedding compositions that can be used are polymeric substances and waxes. The compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and/or emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, or sesame seed oil, glycerol, tetrahydrofurfuryl alcohol, polyethylene glycols or fatty acid esters of sorbitan, or mixtures of these substances, and the like.

Besides such inert diluents, the composition can also include adjuvants, such as wetting agents, emulsifying and/or suspending agents, sweetening, flavoring, or perfuming agents.

Suspensions, in addition to the compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Compositions for rectal or vaginal administration can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration include ointments, powders, sprays and inhalants. The compound or compounds are admixed under sterile conditions with a physiologically acceptable carrier, and any preservatives, buffers, or propellants that may be required. Ophthalmic formulations, eye ointments, powders, and solutions are also contemplated as being within the scope of this invention.

Each of the sulfonylureas, non-sulfonylurea $K^+$ ATP channel blockers, and cAMP phosphodiesterase type 3 inhibitors of the present invention can be administered to a patient at synergistic dosage levels in the range of about 0.1 to about 7,000 mg per day. A preferred dosage range is about 0.1 to about 500 mg per day. The specific dosage and dosage range that can be used for each compound depends on a number of factors, including the requirements of the patient, the severity of the condition or disease being treated, and the pharmacological activity of the compound or compounds being administered. The determination of dosage ranges and optimal dosages for a particular patient is well within the ordinary skill in the art in view of the present disclosure.

Suitable synergistic dosage ranges can be correlated with desired plasma concentrations. For example, an effective plasma concentration of a cAMP phosphodiesterase type 3 inhibitor such as milrinone is about 10 ng/mL to about 10 mg/mL. A preferred plasma concentration is about 100 ng/mL to about 1 mcg/mL. Similarly, an effective plasma concentration for a sulfonylurea such as glyburide is about 5 ng/mL to about 100 mcg/mL. A preferred plasma concentration is 49 ng/mL to about 5 mcg/mL.

The following paragraphs describe exemplary formulations, dosages, etc., useful for non-human patients. The administration of sulfonylureas, non-sulfonylurea $K^+$ ATP channel blockers, and cAMP phosphodiesterase type 3 inhibitors of the present invention can be effected orally or non-orally, for example by injection. An amount of a compound or combination of compounds is administered such that a synergistic dose is received, generally a daily dose which, when administered orally to an animal is usually between 0.01 and 100 mg/kg of body weight, preferably between 0.1 and 50 mg/kg of body weight of each of: a sulfonylurea and/or a non-sulfonylurea $K^+$ ATP channel blocker; and a cAMP phosphodiesterase type 3 inhibitor. It is noted that each of the compounds administered in a combination can have the same or a different dosage. Conveniently, the medication can be carried in the drinking water so that a therapeutic dosage of the combination of compounds is ingested with the daily water supply. The combination of compounds can be directly metered into drinking water, preferably in the form of a liquid, water-soluble concentrate (such as an aqueous solution of a water soluble salt). Conveniently, the compounds of the present invention can also be added directly to the feed, as such, or in the form of an animal feed supplement, also referred to as a premix or concentrate. A premix or concentrate in a carrier is more commonly employed for the inclusion of a compound or compounds in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound or combination of compounds in the finished feed with which the premix is blended. It is important that a compound or combination of compounds be thoroughly blended into the premix and, subsequently, the feed. In this respect, the compound or combination of compounds may be dispersed or dissolved in a suitable oily vehicle such as soybean oil, corn oil, cottonseed oil, and the like, or in a volatile organic solvent and then blended with the carrier. It will be appreciated that the proportions of the compound or combination of compounds in the concentrate are capable of wide variation since the amount of a compound or combination of compounds in the finished feed may be adjusted by blending the appropriate proportion of premix with the feed to obtain the desired level of the compound or compounds.

High potency concentrates may be blended by the feed manufacturer with proteinaceous carrier such as soybean oil meal or other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a synergistic amount of the compounds according to the present invention. The mixtures are thoroughly blended by standard procedures, such as in a twin shell blender, to ensure homogeneity.

If the supplement is used as a top dressing for the feed, it likewise helps to ensure uniformity of distribution of the compound or combination of compounds across the top of the dressed feed.

For parenteral administration in non-human animals, a sulfonylurea and/or non-sulfonylurea $K^+$ ATP channel blocker, and cAMP phosphodiesterase type 3 inhibitor may be prepared in the form of a paste or a pellet and administered as an implant, usually under the skin of the head or ear of the animal.

In general, parenteral administration involves the injection of a sufficient amount of a sulfonylurea, and/or non-sulfonylurea $K^+$ ATP channel blocker, in combination with a cAMP phosphodiesterase type 3 inhibitor to provide the animal with about 0.01 to about 100 mg/kg/day of body weight of each of the active ingredients in the combination.

Paste formulations can be prepared by dispersing the compounds in a pharmaceutically acceptable oil such as peanut oil, sesame oil, corn oil or the like.

Pellets containing an effective amount of compounds of the present invention can be prepared by admixing compounds of the present invention with a diluent such as carbowax, carnauba wax, or the like, and a lubricant, such as magnesium or calcium stearate, can be added to improve the pelleting process.

It is, of course, recognized that more than one pellet may be administered to an animal to achieve the desired dose level. Moreover, it has been found that implants may also be made periodically during the animal treatment period in order to maintain the proper level of compound(s) in the animal's body.

The term pharmaceutically acceptable salts or prodrugs includes the carboxylate salts, amino acid addition salts, and prodrugs of the sulfonylureas, non-sulfonylurea $K^+$ ATP channel blockers, and cAMP phosphodiesterase type 3 inhibitors that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible.

The term "salts" refers to inorganic and organic salts of the sulfonylureas, non-sulfonylurea $K^+$ ATP channel blockers, and cAMP phosphodiesterase type 3 inhibitors. The salts can be prepared in situ during the final isolation and purification, or by separately reacting a purified compound in its free base form with a suitable organic or inorganic acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, or the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al, "Pharmaceutical Salts," *J Pharm Sci*, 66: 1–19 (1977).

Examples of pharmaceutically acceptable, non-toxic esters of the sulfonylureas, non-sulfonylurea $K^+$ ATP channel blockers, and cAMP phosphodiesterase type 3 inhibitors, if applicable, include $C_1$–$C_8$ alkyl esters. Acceptable esters also include $C_5$–$C_7$ cycloalkyl esters, as well as arylalkyl esters such as benzyl. $C_1$–$C_4$ Alkyl esters are preferred. Esters of a sulfonylurea, non-sulfonylurea $K^+$ ATP channel blocker, or cAMP phosphodiesterase type 3 inhibitor may be prepared according to methods that are well known in the art.

Examples of pharmaceutically acceptable non-toxic amides of the sulfonylureas, non-sulfonylurea $K^+$ ATP channel blockers, and cAMP phosphodiesterase type 3 inhibitors include amides derived from ammonia, primary $C_1$–$C_8$ alkyl amines, and secondary $C_1$–$C_8$ dialkyl amines. In the case of secondary amines, the amine may also be in the form of a 5 or 6 membered heterocycloalkyl group containing at least one nitrogen atom. Amides derived from ammonia, $C_1$–$C_3$ primary alkyl amines, and $C_1$–$C_2$ dialkyl secondary amines are preferred. Amides of a sulfonylurea, non-sulfonylurea $K^+$ ATP channel blocker, and cAMP phosphodiesterase type 3 inhibitor may be prepared according to methods well known to those skilled in the art.

The term "prodrug" means compounds that are transformed in vivo to yield a sulfonylurea, non-sulfonylurea $K^+$ ATP channel blocker, and/or cAMP phosphodiesterase type 3 inhibitor. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a sulfonylurea, non-sulfonylurea $K^+$ ATP channel blocker, or a cAMP phosphodiesterase type 3 inhibitor of the invention comprises a carboxylic acid functional group, a prodrug can comprise an ester formed by the replacement of the hydrogen atom of the acid group with a group such as ($C_1$–$C_8$)alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di($C_1$–$C_2$)alkylcarbamoyl-($C_1$–$C_2$)alkyl and piperidino-, pyrrolidino- or morpholino($C_2$–$C_3$)alkyl.

Similarly, if a sulfonylurea, non-sulfonylurea $K^+$ ATP channel blocker, or cAMP phosphodiesterase type 3 inhibitor comprises an alcohol functional group, a prodrug can be formed by the replacement of the hydrogen atom of the alcohol group with a group such as ($C_1$–$C_6$)

alkanoyloxymethyl, 1-(($C_1$–$C_6$)alkanoyloxy)ethyl, 1-methyl-1-(($C_1$–$C_6$)alkanoyloxy)ethyl, ($C_1$–$C_6$)alkoxycarbonyloxymethyl, N-($C_1$–$C_6$)alkoxycarbonylaminomethyl, succinoyl, ($C_1$–$C_6$)alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$–$C_6$)alkyl)$_2$ or glycosyl (the radical resulting from the removal of a hydroxyl group of the hemiacetal form of a carbohydrate).

If a sulfonylurea, non-sulfonylurea $K^+$ ATP channel blocker, or a cAMP phosphodiesterase type 3 inhibitor comprises an amine functional group, a prodrug can be formed by the replacement of a hydrogen atom in the amine group with a group such as R-carbonyl, RO-carbonyl, NRR'-carbonyl where R and R' are each independently ($C_1$–$C_{10}$) alkyl, ($C_3$–$C_7$)cycloalkyl, or benzyl, or R-carbonyl is a natural α-aminoacyl or natural α-aminoacyl-natural α-aminoacyl, —C(OH)C(O)OY wherein Y is H, ($C_1$–$C_6$) alkyl or benzyl, —C(OY$_0$)Y$_1$ wherein Y$_0$ is ($C_1$–$C_4$) alkyl and Y$_1$ is ($C_1$–$C_6$)alkyl, carboxy($C_1$–$C_6$)alkyl, amino ($C_1$–$C_4$)alkyl or mono-N- or di-N,N—($C_1$–$C_6$) alkylaminoalkyl, —C(Y$_2$)Y$_3$ wherein Y$_2$ is H or methyl and Y$_3$ is mono-N- or di-N,N—($C_1$–$C_6$)alkylamino, morpholino, piperidin-1-yl or pyrrolidin-1-yl.

The sulfonylureas, non-sulfonylurea $K^+$ ATP channel blockers, and/or cAMP phosphodiesterase type 3 inhibitors of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if a compound contains a double bond, both the cis and trans forms, as well as mixtures, are contemplated.

Diasteromeric mixtures can be separated into their individual stereochemical components on the basis of their physical chemical differences by methods known per se, for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of this invention may be atropisomers (e.g., substituted biaryls) and are considered as part of this invention.

The sulfonylureas, non-sulfonylurea $K^+$ ATP channel blockers, and/or cAMP phosphodiesterase type 3 inhibitors of the present invention may exist in unsolvated as well as solvated forms with pharmaceutically acceptable solvents such as water, ethanol, and the like. The present invention contemplates and encompasses both the solvated and unsolvated forms.

It is also possible that the sulfonylureas, non-sulfonylurea $K^+$ ATP channel blockers, and/or cAMP phosphodiesterase type 3 inhibitors of the present invention may exist in different tautomeric forms. All tautomers of compounds of the present invention are contemplated.

It is also intended that the invention disclosed herein encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, 35S, $^{18}$F, and $^{36}$Cl, respectively. Compounds of the present invention that contain the aforementioned isotopes and/or other isotopes of other atoms are within the scope of this invention. Certain isotopically labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention and prodrugs thereof can generally be prepared by substituting a readily available isotopically labelled reagent for a non-isotopically labelled reagent.

Non-insulin dependent diabetes mellitus (also called Type 2 or adult onset diabetes), insulin resistance, impaired glucose tolerance, Syndrome X, hyperglycemia, polycystic ovary syndrome, cataracts, or any of the diabetic complications such as neuropathy, nephropathy, retinopathy, or cardiomyopathy can be treated by administering to a patient having or at risk of having one of the above-mentioned diseases a synergistic amount of: 1) a sulfonylurea and/or a non-sulfonylurea $K^+$ ATP channel blocker; and 2) a cAMP phosphodiesterase type 3 inhibitor. It is also contemplated that non-insulin dependent diabetes mellitus, insulin resistance, impaired glucose tolerance, Syndrome X, hyperglycemia, polycystic ovary syndrome, or cataracts, or any of the diabetic complications such as neuropathy, nephropathy, retinopathy, or cardiomyopathy can be treated by administering to a patient having or at risk of having one of the above-mentioned diseases a synergistic amount a sulfonylurea and/or a non-sulfonylurea $K^+$ ATP channel blocker, and a cAMP phosphodiesterase type 3 inhibitor and another agent that can be used to treat non-insulin dependent diabetes mellitus, insulin resistance, impaired glucose tolerance, Syndrome X, hyperglycemia, polycystic ovary syndrome, or cataracts, or any of the diabetic complications such as neuropathy, nephropathy, retinopathy, or cardiomyopathy.

Representative examples of additional agents that can be used include insulin and insulin analogs (e.g. LysPro insulin); GLP-1 (7-37) (insulinotropin) and GLP-1 (7-36)-NH$_2$; biguanides: mefformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, rosiglitazone; PPAR-gamma agonists; fatty acid oxidation inhibitors: clomoxir, etomoxir; a-glucosidase inhibitors: acarbose, miglitol, emiglitate, voglibose, MDL-25,637, camiglibose, MDL-73,945; β-agonists: BRL 35135, BRL 37344, Ro 16-8714, ICI D7114, CL 316,243; lipid-lowering agents: benfluorex; antiobesity agents: fenfluramine; vanadate and vanadium complexes (e.g. Naglivan®) and peroxovanadium complexes; amylin antagonists; glucagon antagonists; gluconeogenesis inhibitors; somatostatin agonists and antagonists; antilipolytic agents: nicotinic acid, acipimox, WAG 994. Any combination of agents can be administered as described above.

Preferred compounds from the above classes include: LysPro insulin; GLP-1 (7-37) (insulinotropin); GLP-1 (7-36)-NH$_2$; metformin; phenformin; buformin; midaglizole; isaglidole; deriglidole; idazoxan; efaroxan; fluparoxan; linogliride; ciglitazone; pioglitazone; englitazone; troglitazone; darglitazone; rosiglitazone; clomoxir; etomoxir; acarbose; miglitol; emiglitate; voglibose; MDL-25,637; camiglibose; MDL-73,945; BRL 35135; BRL 37344; Ro 16-8714; ICI D7114; CL 316,243; benfluorex; fenfluramine; Naglivan®; acipimox; WAG 994; Symlin™; or AC2993.

In addition to the categories and compounds mentioned above, the sulfonylureas, non-sulfonylurea K$^+$ ATP channel blockers, and cAMP phosphodiesterase type 3 inhibitors of the present invention can be administered in combination with thyromimetic compounds, aldose reductase inhibitors, glucocorticoid receptor antagonists, NHE-1 inhibitors, or sorbitol dehydrogenase inhibitors, or combinations thereof, to treat diabetes, insulin resistance, Syndrome X, diabetic neuropathy, diabetic nephropathy, diabetic retinopathy, diabetic cardiomyopathy, polycystic ovary syndrome, cataracts, hyperglycemia, hypercholesterolemia, hypertension, hyperlipidemia, atherosclerosis, or tissue ischemia, particularly myocardial ischemia, and impaired glucose tolerance.

It is also contemplated that the combinations of sulfonylureas, and/or non-sulfonylurea K$^+$ ATP channel blockers, and cAMP phosphodiesterase type 3 inhibitors described herein may be used to treat hypercholesterolemia, hypertension, hyperlipidemia, atherosclerosis, or tissue ischemia, particularly myocardial ischemia, which are diseases that occur more frequently in diabetic patients than in non-diabetic patients.

In addition, it is contemplated that the combinations of sulfonylureas, and/or non-sulfonylurea K$^+$ ATP channel blockers, and cAMP phosphodiesterase type 3 inhibitors described herein that may be used to treat hypercholesterolemia, hypertension, hyperlipidemia, atherosclerosis, or tissue ischemia, particularly myocardial ischemia, can be used in combination with other compounds that are used to treat hypercholesterolemia, hypertension, hyperlipidemia, atherosclerosis, or tissue ischemia, particularly myocardial ischemia.

It is generally accepted that thyroid hormones, specifically, biologically active iodothyronines, are critical to normal development and to maintaining metabolic homeostasis. Thyroid hormones stimulate the metabolism of cholesterol to bile acids and enhance the lipolytic responses of fat cells to other hormones. U.S. Pat. Nos. 4,766,121; 4,826,876; 4,910,305; and 5,061,798 disclose certain thyroid hormone mimetics (thyromimetics), namely, 3,5-dibromo-3'-[6-oxo-3(1H)-pyridazinylmethyl]-thyronines. U.S. Pat. No. 5,284,971 discloses certain thyromimetic cholesterol lowering agents, namely, 4-(3-cyclohexyl-4-hydroxy or -methoxy phenylsulfonyl)-3,5 dibromo-phenylacetic compounds. U.S. Pat. Nos. 5,401,772; 5,654, 468; and 5,569,674 disclose certain thyromimetics that are lipid lowering agents, namely, heteroacetic acid derivatives. In addition, certain oxamic acid derivatives of thyroid hormones are known in the art. For example, N. Yokoyama, et al. in an article published in the *Journal of Medicinal Chemistry*, 38 (4): 695–707 (1995) describe replacing a —CH$_2$ group in a naturally occurring metabolite of T$_3$ with an —NH group resulting in —HNCOCO$_2$H. Likewise, R. E. Steele et al. in an article published in International Congressional Service (*Atherosclerosis X*) 1066: 321–324 (1995) and Z. F. Stephan et al. in an article published in *Atherosclerosis*, 126: 53–63 (1996), describe certain oxamic acid derivatives useful as lipid-lowering thyromimetic agents, yet devoid of undesirable cardiac activities.

Each of the thyromimetic compounds referenced above and other thyromimetic compounds can be used in combination with the sulfonylureas, and/or non-sulfonylurea K$^+$ ATP channel blockers, and cAMP phosphodiesterase type 3 inhibitors of the present invention to treat diabetes, insulin resistance, Syndrome X diabetic neuropathy, diabetic nephropathy, diabetic retinopathy, diabetic cardiomyoapthy, polycystic ovary syndrome, cataracts hyperglycemia, hypercholesterolemia, hypertension, hyperlipidemia, atherosclerosis, tissue ischemia or impaired glucose tolerance.

The sulfonylureas, and/or non-sulfonylurea K$^+$ ATP channel blockers, and cAMP phosphodiesterase type 3 inhibitors of the present invention can also be used in combination with aldose reductase inhibitors. Aldose reductase inhibitors constitute a class of compounds that have become widely known for their utility in preventing and treating conditions arising from complications of diabetes, such as diabetic neuropathy and nephropathy. Such compounds are well known to those skilled in the art and are readily identified by standard biological tests. For example, the aldose reductase inhibitors zopolrestat, 1-phthalazineacetic acid, 3,4-dihydro-4-oxo-3-[[5-(trifluoromethyl)-2-benzothiazolyl]methyl]-, and related compounds are described in U.S. Pat. No. 4,939,140.

Aldose reductase inhibitors have been taught for use in lowering lipid levels in mammals. See, for example, U.S. Pat. No. 4,492,706 and EP 0 310 931 A2.

U.S. Pat. No. 5,064,830 discloses the use of certain oxophthalazinyl acetic acid aldose reductase inhibitors, including zopolrestat, for lowering of blood uric acid levels.

Commonly assigned U.S. Pat. No. 5,391,551 discloses the use of certain aldose reductase inhibitors, including zopolrestat, for lowering blood lipid levels in humans. The disclosure teaches that therapeutic utilities derive from the treatment of diseases caused by an increased level of triglycerides in the blood, such diseases include cardiovascular disorders such as thrombosis, arteriosclerosis, myocardial infarction, and angina pectoris. A preferred aldose reductase inhibitor is zopolrestat.

The term aldose reductase inhibitor refers to compounds that inhibit the bioconversion of glucose to sorbitol, which is catalyzed by the enzyme aldose reductase.

Any aldose reductase inhibitor may be used in a combination with the sulfonylureas, and/or non-sulfonylurea K$^+$ ATP channel blockers, and cAMP phosphodiesterase type 3 inhibitors of the present invention. Aldose reductase inhibition is readily determined by those skilled in the art according to standard assays (J. Malone, *Diabetes*, 29:861–864 (1980). "Red Cell Sorbitol, an Indicator of Diabetic Control"). A variety of aldose reductase inhibitors are described herein; however, other aldose reductase inhibitors useful in the compositions and methods of this invention will be known to those skilled in the art.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose).

Accordingly, examples of aldose reductase inhibitors useful in the present invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl] thioxomethyl]-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. No. 4,464, 382, U.S. 4,791,126, U.S. 4,831,045);
4. 3-(4-bromo-2-fluorobenzyl)-7-chloro-3,4-dihydro-2,4-dioxo-1 (2H)-quinazolineacetic acid (zenarestat, U.S. Pat. Nos. 4,734,419, and 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. Nos. 5,270,342 and U.S. 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)2',5'-dione (U.S. Pat. No. 4,438,272);
13. 2,7-di-fluoro-spiro(9H-fluorene-9,4'-imidazolidine)2', 5'-dione (U.S. Pat. Nos. 4,436,745, U.S. 4,438,272);
14. 2,7-di-fluoro-5-methoxy-spiro(9H-fluorene-9,4'-imidazolidine)2',5'-dione (U.S. Pat. Nos. 4,436,745, U.S. 4,438,272);
15. 7-fluoro-spiro(5H-indenol[1,2-b]pyridine-5,3'-pyrrolidine)2,5'-dione (U.S. Pat. Nos. 4,436,745, U.S. 4,438,272);
16. d-cis-6'-chloro-2',3'-dihydro-2'-methyl-spiro-(imidazolidine-4,4'4'-H-pyrano(2,3-b)pyridine)-2,5-dione (U.S. Pat. No. 4,980,357);
17. spiro[imidazolidine-4,5'(6H)-quinoline]2,5-dione-3'-chloro-7',8'-dihydro-7'-methyl-(5'-cis)(U.S. Pat. No. 5,066,659);
18. (2S,4S)-6-fluoro-2',5'-dioxospiro(chroman-4,4'-imidazolidine)-2-carboxamide (U.S. Pat. No. 5,447, 946);
19. 2-[(4-bromo-2-fluorophenyl)methyl]-6-fluorospiro [isoquinoline-4(1 H),3'-pyrrolidine]-1,2',3,5'(2H)-tetrone (ARI-509, U.S. Pat. No. 5,037,831);
20. 3,4-dihydro-3-(5-fluorobenzothiazol-2-ylmethyl)-4-oxophthalazin-1-yl-acetic acid;
21. 3-(5,7-difluorobenzoxazol-2-ylmethyl)-3,4-dihydro-4-oxophthalazin-1-ylacetic acid;
22. 3-(5-chlorobenzothiazol-2-ylmethyl)-3,4-dihydro-4-oxophthalazin-1-ylacetic acid;
23. 3-(5,7-dichlorobenzothiazol-2-ylmethyl)-3,4-dihydro-4-oxophthalazin-1-ylacetic acid;
24. 3,4-dihydro-4-oxo-3-(5-trifluoromethylbenzoxazol-2-ylmethyl)phthalazin-1-ylacetic acid;
25. 3,4-dihydro-3-(5-fluorobenzoxazol-2-ylmethyl)-4-oxophthalazin-1-yl-acetic acid;
26. 3-(5,7-difluorobenzoxazol-2-ylmethyl)-3,4-dihydro-4-oxophthalazin-1-ylacetic acid;
27. 3-(5-chlorobenzoxazol-2-ylmethyl)-3,4-dihydro-4-oxophthalazin-1-ylacetic acid;
28. 3-(5,7-dichlorobenzoxazol-2-ylmethyl)-3,4-dihydro-4-oxophthalazin-1-ylacetic acid; and
29. zopolrestat; 1-phthalazineacetic acid, 3,4-dihydro-4-oxo-3-[[5-(trifluoromethyl)-2-benzothiazolyl]methyl]-.

Procedures for making the aldose reducatase inhibitors 20–29 can be found in PCT publication number WO 99/26659.

Each of the aldose reductase inhibitors referenced above and other aldose reductase inhibitors can be used in combination with the sulfonylureas, and/or non-sulfonylurea $K^+$ ATP channel blockers, and cAMP phosphodiesterase type 3 inhibitors of the present invention to treat diabetes, insulin resistance, Syndrome X, diabetic neuropathy, diabetic nephropathy, diabetic retinopathy, diabetic cardiomyopathy, polycystic ovary syndrome, cataracts, hyperglycemia, hypercholesterolemia, hypertension, hyperlipidemia, atherosclerosis, tissue ischemia, or impaired glucose tolerance.

The sulfonylureas, and/or non-sulfonylurea $K^+$ ATP channel blockers, and cAMP phosphodiesterase type 3 inhibitors of the present invention can also be used in combination with glucocorticoid receptor antagonists. The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-β. Such interactions result in inhibition of API- and NFκ-β-mediated transcription and are believed to be responsible for the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist. GR antagonists can be used in the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty. Examples or GR antagonists that can be used in combination with a compound of the present invention include the compounds disclosed in U.S. provisional patent application No. 60/132,130.

Each of the glucocorticoid receptor antagonists referenced above and other glucocorticoid receptor antagonists can be used in combination with the sulfonylureas, and/or non-sulfonylurea $K^+$ ATP channel blockers, and cAMP phosphodiesterase type 3 inhibitors of the present invention to treat diabetes, insulin resistance, Syndrome X, diabetic neuropathy, diabetic nephropathy, diabetic retinopathy, diabetic cardiomyopathy, polycystic ovary syndrome, cataracts, hyperglycemia, hypercholesterolemia, hypertension, hyperlipidemia, atherosclerosis, tissue ischemia, or impaired glucose tolerance.

The sulfonylureas, and/or non-sulfonylurea $K^+$ ATP channel blockers, and cAMP phosphodiesterase type 3 inhibitors of the present invention can also be used in combination with sorbitol dehydrogenase inhibitors. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and a method for treating or preventing diabetic complications by inhibiting the enzyme sorbitol dehydrogenase.

Each of the sorbitol dehydrogenase inhibitors referenced above and other sorbitol dehydrogenase inhibitors can be used in combination with the sulfonylureas, and/or non-sulfonylurea $K^+$ ATP channel blockers, and cAMP phosphodiesterase type 3 inhibitors of the present invention to treat diabetes, insulin resistance, Syndrome X, diabetic neuropathy, diabetic nephropathy, diabetic retinopathy, diabetic cardiomyopathy, polycystic ovary syndrome, cataracts, hyperglycemia, hypercholesterolemia, hypertension, hyperlipidemia, atherosclerosis, tissue ischemia, or impaired glucose tolerance.

The sulfonylureas, and/or non-sulfonylurea $K^+$ ATP channel blockers, and CAMP phosphodiesterase type 3 inhibitors of the present invention can also be used in combination with sodium-hydrogen exchanger type 1 (NHE-1) inhibitors. NHE-1 inhibitors can be used to reduce tissue damage resulting from ischemia. Of great concern is tissue damage that occurs as a result of ischemia in cardiac, brain, liver, kidney, lung, gut, skeletal muscle, spleen, pancreas, nerve, spinal cord, retina tissue, the vasculature, or intestinal tissue. NHE-1 inhibitors can also be administered to prevent perioperative myocardial ischemic injury. Examples of NHE-1 inhibitors include those disclosed in PCT patent application number PCT/IB99/00206.

Each of the NHE-1 inhibitors referenced above and other NHE-1 inhibitors can be used in combination with the sulfonylureas, and/or non-sulfonylurea $K^+$ ATP channel blockers, and cAMP phosphodiesterase type 3 inhibitors of the present invention to treat diabetes, insulin resistance, Syndrome X, diabetic neuropathy, diabetic nephropathy, diabetic retinopathy, diabetic cardiomyopathy, polycystic ovary syndrome, cataracts, hyperglycemia, hypercholesterolemia, hypertension, hyperlipidemia, atherosclerosis, tissue ischemia, or impaired glucose tolerance.

The examples presented below are intended to illustrate particular embodiments of the invention, and are not intended to limit the scope of the specification, including the claims, in any manner. All patents, patent applications, and other references cited in this application are hereby incorporated by reference.

EXAMPLES

Measurement of Insulin Secretion from INS-1 Cells

The INS-1 cell is a β-cell line derived from an X-ray induced transplantable rat insulinoma. Asfari, M. et al., *Endocrinology*, 130:167–178 (1992). When maintained in cell culture, the cells of this line secrete insulin in response to the same stimuli that stimulate insulin secretion from the β-cells present in the intact islet of Langerhans. The cells are grown until confluent in 24-well tissue culture plates in a standard tissue culture medium [RPMI1640 without L-glutamine (Gibco, Rockville, Md.) containing: 10% fetal bovine serum (Gibco), 1% penicillin/streptomycin (Gibco), 1% L-glutamine (Gibco), 10 mM sodium HEPES buffer (Gibco) pH 7.4,1 mM sodium pyruvate (Sigma, St. Louis) and 50 $\mu$M 2-mercaptoethanol (Sigma).

Secretion of insulin from these cells was measured as follows. The incubation medium was removed from the confluent cell monolayers by aspiration and replaced with Kreb's-Ringer bicarbonate (KRB) buffer without glucose, but containing 0.1% bovine serum albumin (BSA). The cells were incubated for 2 hours in this medium in a humidified 37° C. incubator filled with air with 5% $CO_2$ by volume added. The pre-incubation medium was then removed by aspiration and replaced with KRB buffer (pH 7.4) containing 0.1% BSA, and glucose and stimulatory compounds at the desired concentrations. The plates were returned to the incubator for four hours. At the end of this time, aliquots of the buffer were collected from each well and the insulin concentration present was measured by radioimmunoassay (Linco Research, Inc., St. Louis, Mo.).

Measurement of Insulin Secretion from Rat Islets

Rat islets of Langerhans were prepared from the pancreata of normal Sprague-Dawley rats by an adaptation of a published method. Lacy, P. E. et al., *Diabetes*, 16:35–39 (1967). This method is described below.

Rats were anaesthetized by intraperitoneal administration of 35–50 mg/kg of pentobarbital. The abdominal cavity was opened and approximately 15ml of a buffered solution of collagenase introduced into the pancreatic duct via a needle. The solution comprised 3 mg/ml collagenase in magnesium-free Hanks buffer (127 mM NaCl, 20 mM HEPES, 5.4 mM KCl, 0.34 mM $Na_2HPO_4$, 1 mM $KH_2PO_4$, 1.19 mM $CaCl_2$, pH 7.4). The pancreas was then dissected free of connective tissue, excised from the body and minced with scissors in a beaker containing additional collagenase buffer as described above. The pancreatic tissue was then further digested by incubating it with stirring at 37° C. in the collagenase buffer for 10–15 minutes. The tissue was then transferred to two 16×125 mm tubes and centrifuged very briefly to settle the solid material. Half of each supernatant was removed and replaced with magnesium-free Hanks buffer without collagenase. The tubes were shaken vigorously by hand and then centrifuged as before. The wash, shake and centrifuge procedure was then repeated twice. The pancreatic digest was then washed 4 more times with magnesium-free Hanks buffer, pouring off all of the supernatant after each centrifugation step and omitting the shaking. After the final wash, the pellets were mixed with 4 ml of a 27% (w/v) solution of Ficoll (Sigma, St. Louis, Mo.) in magnesium-free Hanks buffer and transferred to 30 ml tubes. A 4 ml volume of 23%

(w/v) Ficoll in magnesium-free Hanks buffer was layered on top followed by 4 ml of 20.5% Ficoll in magnesium-free Hanks buffer and 4 ml of 11% Ficoll in magnesium-free Hanks buffer. The tubes were centrifuged for 10 minutes at 250×g. Islets were collected from the 11%/20.5% and 20.5%/23% interfaces and placed in 50 ml tubes. They were washed twice with Hanks buffer containing magnesium (127 mM NaCl, 20 mM HEPES, 5.4 mM KCl, 0.34 mM $Na_2HPO_4$, 1 mM $KH_2PO_4$, 0.81 mM $MgSO_4$, 1.19 mM $CaCl_2$, pH 7.4), sedimenting the islets by centrifugation for 10 minutes at 250×g between washes. After the last centrifugation step, the pellet was transferred to a petri dish and the islets manually transferred from the dish to an appropriate culture vessel using a 200 $\mu$l constriction pipette.

Once the islets were separated from residual non-islet tissue, they were either used immediately or maintained in a standard tissue culture medium [RPMI1640 medium (Gibco) containing 10% fetal bovine serum (Gibco), 1% antibiotic/antimycotic (Gibco) and 22 mM glucose].

Insulin secretion in response to stimulation was measured as follows. Islets were transferred to Kreb's-Ringer bicarbonate (KRB) buffer pH 7.4 containing 2.8mM glucose and 0.1% bovine serum albumin (Sigma) and placed for two hours in a humidified 37° C. incubator filled with air to which 5% $CO_2$ by volume was added. After the pre-incubation, islets were transferred to a 48 well tissue culture plate (8 islets per well) containing KRB buffer, 0.1% bovine serum albumin, and glucose and stimulatory compounds at the desired concentrations in the buffer composition. The plates were returned to the incubator for two hours. At the end of this time, aliquots of the buffer were collected from each well and the insulin concentration present was measured by radioimmunoassay (Linco Research, Inc., St. Louis, Mo.).

In Vitro Insulin Secretion Assay and Statistical Analysis

Data from in vitro experiments in the INS-1 cell assay described above combining glyburide and milrinone for induction of insulin secretion were analyzed. A total of 399 data points from six experiments were collected. The response is the amount of insulin secretion at various combinations of different concentrations of glyburide and milrinone. The response data from each experiment was normalized by the concentration of cells of β-cell lines in plates for the experiment. The data from the six experiments were then combined in the statistical analysis.

Figure 1:
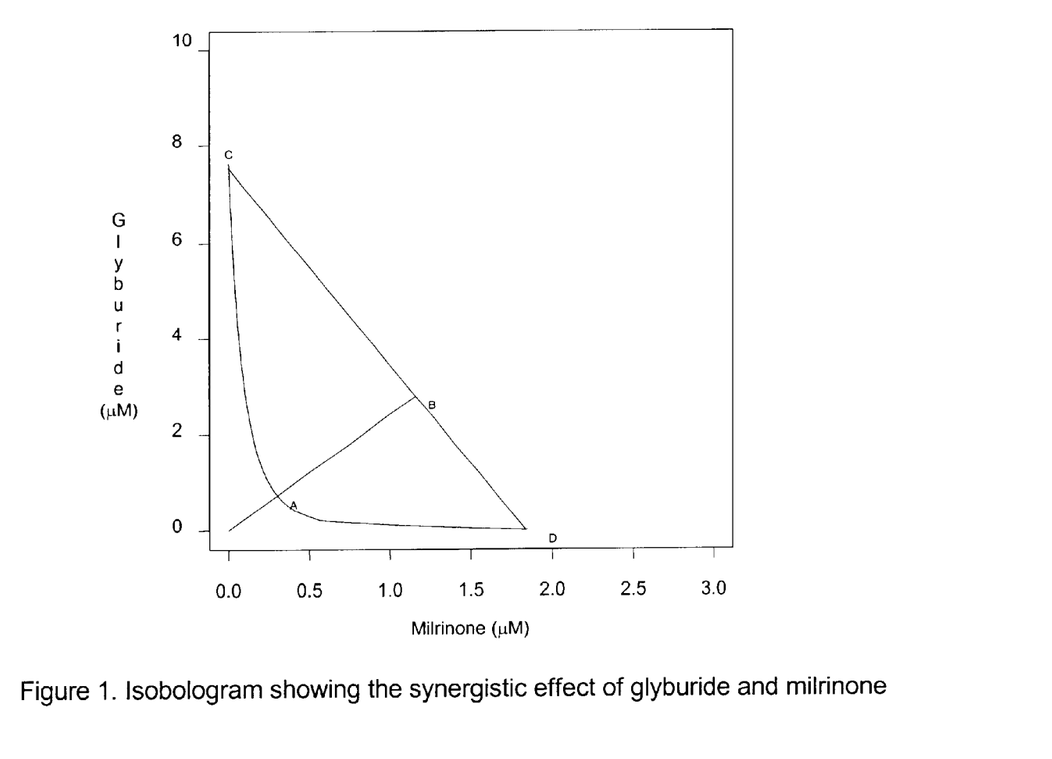
FIG. 1 is an isobologram that shows the synergistic effect of combinations of milrinone and glyburide on insulin secretion.

A response surface was constructed from the combined data. From the response surface, a contour line corresponding to 95% of the maximum response level due to glyburide alone was obtained. This contour line is shown in FIG. 1. The contour line represents all the combinations of the two drugs that produce this fixed amount of response based on the data from the experiments. The plot in FIG. 1 is called an isobologram. Isobolograms are used in the study of synergism and are well known to those skilled in the art. If only an additive effect exists, the contour line would be a straight line connecting points C and D. Synergism exists if the actual contour is below the straight line.

The magnitude of the synergistic effect is measured by how far the contour line is from the straight line. The line representing a fixed ratio of the two drugs is a straight line that goes through the origin in FIG. 1. This line intercepts the contour at point A and the additive straight line at point B. For a given ratio of the two drugs, we assess the magnitude of synergistic effect by a dose reduction factor r defined as:

$$r = \frac{\text{Amount of Glyburide at } A}{\text{Amount of Glyburide at } B} = \frac{\text{Amount of Milrinone at } A}{\text{Amount of Milrinone at } B}.$$

The points C and D represent the equivalent concentrations for glyburide and milrinone, respectively. If we define C and D as one unit for glyburide and milrinone, respectively, then the dose reduction factor r represents the fraction of the combined drugs needed to achieve the same level of response achieved by one unit of either drug individually. So if r is smaller than 1, then synergism exists. The smaller the r, the stronger the synergistic effect. It is possible to mathematically determine the ratio that produced the biggest synergistic effect and the dose reduction factor r associated with the ratio. We found that the ratio is glyburide/milrinone=2.4, and the corresponding dose reduction factor r is 0.259. The implication is that with this ratio of the two drugs, only 0.259 of one unit of the combined amount of glyburide and milrinone is needed to produce the same amount of response corresponding to one unit of either glyburide or milrinone alone. FIG. 1 shows that for a wide range of ratios synergism exists.

Since the contour line, as well as the dose reduction factor r is derived from data, they are subject to uncertainties associated with the data. The uncertainties come from factors such as measurement errors, β-cell line variations, and other random factors. When an observed dose reduction factor r is less than 1, the main objective of the statistical analysis is to determine whether it is real or it is due to random chance. This is accomplished by first calculating the standard error of r, sd(r), and then calculating the probability of having a dose reduction factor no greater than the observed according to a normal distribution with mean 1 and standard deviation sd(r). This probability is the p-value. If the p-value is less than 0.05, we conclude that the synergistic effect is statistically significant. Table 1 lists the dose the associated p-value for each of the selected ratios of the two or each of the selected ratios, the synergistic effect is significant.

TABLE 1

Summary of Statistical Analysis Results

| Glyburide/Milrinone | r | sd(r) | p-value |
|---|---|---|---|
| 0.003 | 0.873 | 0.0236 | 3.45E-08 |
| 0.01 | 0.741 | 0.0358 | 2.15E-13 |
| 0.03 | 0.598 | 0.0404 | 1.08E-23 |
| 0.1 | 0.452 | 0.0379 | 9.10E-48 |
| 0.3 | 0.348 | 0.0301 | 3.39E-104 |
| 1 | 0.276 | 0.0195 | 2.59E-302 |
| 2.4 | 0.259 | 0.0256 | 4.78E-185 |
| 3 | 0.26 | 0.0305 | 2.95E-130 |
| 10 | 0.314 | 0.0711 | 2.46E-22 |
| 30 | 0.44 | 0.113 | 3.78E-07 |
| 100 | 0.64 | 0.129 | 0.00272 |
| 300 | 0.814 | 0.0964 | 0.0266 |

From the statistical analysis, we conclude that over a wide range of ratios of combinations of the two drugs, the synergistic effect is statistically significant. We also found that the ratio of the two drugs that produced the maximum synergistic effect is glyburide/milrinone=2.4. With this ratio, only 0.259 of one unit of the combined amount of glyburide and milrinone was needed to produce the same amount of response corresponding to one unit of either glyburide or milrinone alone. It is noted that the absolute concentration of milrinone was in the range of about 1 to about 100 micromolar and in the range of about 0.1 to about 10 micromolar for glyburide. Various concentrations of each drug that corresponded to a particular ratio were tested.

What is claimed is:

1. A method of inducing insulin secretion in vitro, the method comprising the step of treating an insulin-secreting cell line with a synergistic amount of: 1) a sulfonylurea that stimulates insulin secretion; and 2) a cAMP phosphodiesterase type 3 inhibitor, thereby increasing insulin secretion of the cell line.

2. The method of claim 1 wherein the cAMP phosphodiesterase type 3 inhibitor is a selective cAMP phosphodiesterase type 3B inhibitor.

3. The method of claim 1 wherein the sulfonylurea is glyburide, chlorpropamide, glibenclamide, glipizide, gliclazide, glimepiride, tolbutamide, acetohexamide, or tolazamide.

4. The method of claim 1 wherein the sulfonylurea is glipizide or glyburide.

5. The method of claim 1 wherein the sulfonylurea is glyburide.

6. The method of claim 1 wherein the cAMP phosphodiesterase type 3 inhibitor is milrinone, amrinone, enoximone, indolidan, cilostamide, lixazinone, imazodan, cilostazol, bemorandan, siguazodan, adibendan, pimobendan, saterinone, sulmazole or vesnarinone.

7. The method of claim 1 wherein the cAMP phosphodiesterase type 3 inhibitor is milrinone.

8. The method of claim 1 wherein the CAMP phosphodiesterase type 3 inhibitor is milrinone and the sulfonylurea is glyburide.

* * * * *